United States Patent
Ptock et al.

(10) Patent No.: US 7,449,195 B2
(45) Date of Patent: Nov. 11, 2008

(54) FUNGICIDE MIXTURES

(75) Inventors: Arne Ptock, Ludwigshafen (DE);
Eberhard Ammermann, Heppenheim (DE); Reinhard Stierl, Mutterstadt (DE); Gisela Lorenz, Hambach (DE); Siegfried Strathmann, Limburgerhof (DE); Maria Scherer, Landau (DE); Klaus Schelberger, Gönnheim (DE); Achim Reddig, Landau (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 832 days.

(21) Appl. No.: 10/466,397

(22) PCT Filed: Jan. 19, 2002

(86) PCT No.: PCT/EP02/00497

§ 371 (c)(1),
(2), (4) Date: Jul. 16, 2003

(87) PCT Pub. No.: WO02/056690

PCT Pub. Date: Jul. 25, 2002

(65) Prior Publication Data

US 2004/0053980 A1    Mar. 18, 2004

(30) Foreign Application Priority Data

Jan. 22, 2001    (DE) .............................. 101 02 835

(51) Int. Cl.
| A01N 25/00 | (2006.01) |
| A01N 25/32 | (2006.01) |
| A01N 63/00 | (2006.01) |
| A01N 43/78 | (2006.01) |
| A01N 43/50 | (2006.01) |
| A01N 47/10 | (2006.01) |
| A61K 31/415 | (2006.01) |
| A61K 31/27 | (2006.01) |

(52) U.S. Cl. ...................... 424/405; 424/406; 514/385; 514/396; 514/479; 504/118; 504/267; 504/275; 504/303

(58) Field of Classification Search .................. 424/405, 424/406; 514/385, 396, 479; 504/118, 267, 504/275, 303
See application file for complete search history.

(56) References Cited

U.S. PATENT DOCUMENTS

| 5,210,084 A | 5/1993 | Wollweber et al. |
| 5,411,987 A | 5/1995 | Wollweber et al. |
| 5,420,148 A | 5/1995 | Dehne et al. |
| 5,491,165 A | 2/1996 | Dehne et al. |
| 5,504,100 A | 4/1996 | Dehne et al. |

(Continued)

FOREIGN PATENT DOCUMENTS

| DE | 43 21 897 | 1/1995 |
| DE | 195 31 814 | 3/1997 |
| DE | 199 04 081 | 8/2000 |
| DE | 100 21 412 A1 * | 6/2001 |
| EP | 298 196 | 1/1989 |
| EP | 398 072 | 11/1990 |

(Continued)

OTHER PUBLICATIONS

Kosman et al. "Procedure for caculating and differentiating synergism and antagonism in action of fungicide mixtures," Phytopathology, 1996, vol. 86, No. 11, pp. 1263-1272.*

(Continued)

*Primary Examiner*—Shengjun Wang
(74) *Attorney, Agent, or Firm*—Novak Druce + Quigg LLP

(57) ABSTRACT

Fungicidal mixtures, comprising
A) imidazole derivatives of the formula I

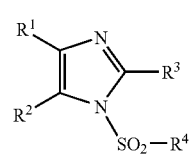

in which $R^1$ and $R^2$ are halogen or phenyl, which may be substituted by halogen or alkyl, or $R^1$ and $R^2$ together with the bridging C=C double bond form a 3,4-difluoromethylenedioxyphenyl group; $R^3$ is cyano or halogen, and $R^4$ is dialkylamino or isoxazol-4-yl, which may carry two alkyl radicals; and
B) valinamides of the formula II,

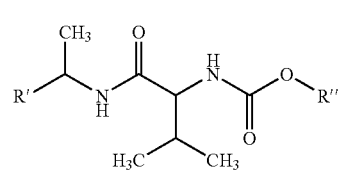

in which
R' is phenyl, which is substituted in the 4-position by halogen, $C_1$-$C_4$-alkyl or $C_1$-$C_4$-alkoxy,
  is 1- or 2-naphthyl, or
  is benzothiazol-2-yl, which is substituted in the 6-position by halogen; and
R" is $C_3$-$C_4$-alkyl;
in a synergistically effective amount, methods for controlling harmful fungi using mixtures of the compounds I and II and the use of the compounds I and the compounds II for preparing such mixtures are described.

5 Claims, No Drawings

U.S. PATENT DOCUMENTS

| | | | |
|---|---|---|---|
| 5,504,109 A | 4/1996 | Seitz et al. | |
| 5,516,786 A | 5/1996 | Wollweber et al. | |
| 5,577,976 A | 11/1996 | Haka | |
| 5,585,393 A | 12/1996 | Dehne et al. | |
| 5,650,423 A | 7/1997 | Dehne et al. | |
| 5,668,163 A | 9/1997 | Dehne et al. | |
| 5,847,194 A | 12/1998 | Wetterich et al. | |
| 5,922,899 A | 7/1999 | Wetterich et al. | |
| 6,020,354 A | 2/2000 | Assmann et al. | |
| 6,057,363 A | 5/2000 | Dehne et al. | |
| 6,127,547 A | 10/2000 | Assmann et al. | |
| 6,160,001 A | 12/2000 | Assmann et al. | |
| 6,245,772 B1 | 6/2001 | Dehne et al. | |
| 6,268,508 B1 | 7/2001 | Assmann et al. | |
| 6,297,236 B1 | 10/2001 | Stenzel et al. | |
| 6,375,965 B1 * | 4/2002 | Matsuo et al. | 424/405 |
| 6,436,979 B1 | 8/2002 | Schelberger | |
| 6,444,693 B1 | 9/2002 | Wachendorff-Neumann et al. | |
| 6,624,183 B2 * | 9/2003 | Wachendorff-Neumann et al. | 514/367 |
| 2001/0006964 A1 | 7/2001 | Dehne et al. | |
| 2002/0072535 A1 | 6/2002 | Stenzel | |

FOREIGN PATENT DOCUMENTS

| | | |
|---|---|---|
| EP | 610 764 | 8/1994 |
| EP | 630 570 | 12/1994 |
| JP | 9 323984 | 12/1997 |
| JP | 2001-89305 | 4/2001 |
| JP | 2001-181114 | 7/2001 |
| WO | 97/06171 | 2/1997 |
| WO | 98/47370 | 10/1998 |
| WO | 99/56551 | 11/1999 |
| WO | 01/05231 | 1/2001 |

OTHER PUBLICATIONS

Derwent 95-044221/07.
Derwent 98-095679/09.
Mitsuyoshi et al., "Agricultural and Horticultural Bactericide Composition;" English language abstract and Table 1 of reference BA.
English language translation of Office action issued in Japanese counterpart application on Jan. 22, 2008.

* cited by examiner

FUNGICIDE MIXTURES

The present invention relates to fungicidal mixtures, comprising

A) imidazole derivatives of the formula I

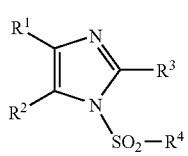

in which $R^1$ and $R^2$ are halogen or phenyl, which may be substituted by halogen or $C_1$-$C_4$-alkyl, or $R^1$ and $R^2$ together with the bridging C=C double bond form a 3,4-difluoromethylenedioxyphenyl group;

$R^3$ is cyano or halogen, and $R^4$ is di($C_1$-$C_4$-alkyl)amino or isoxazol-4-yl, which may carry two $C_1$-$C_4$-alkyl radicals; and B) valinamides of the formula II,

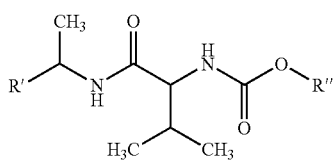

in which

R' is phenyl, which is substituted in the 4-position by halogen or $C_1$-$C_4$-alkyl or $C_1$-$C_4$-alkoxy,
is 1- or 2-naphthyl, or
is benzothiazol-2-yl, which is substituted in the 6-position by halogen; and R" is $C_3$-$C_4$-alkyl;

in a synergistically effective amount.

Moreover, the invention relates to methods for controlling harmful fungi using mixtures of the compounds I and II and to the use of the compounds I and the compounds II for preparing such mixtures.

The imidazole derivatives of the formula I, their preparation and their action against harmful fungi are known from the literature (EP-A 298 196, WO-A 97/06171).

The valinamides of the formula II and processes for their preparation are described in EP-A-0 398 072, EP-A-0 610 764, DE-A-43 21 897, WO-A-96/07638 and JP-A 09/323984. Moreover, they can be prepared similarly to the processes described in DE 1 95 31 814.

It is an object of the present invention to provide mixtures which have an improved activity against harmful fungi combined with a reduced total amount of active compounds applied (synergistic mixtures), with a view to reducing the application rates and improving the activity spectrum of the known compounds I and II.

We have found that this object is achieved by the mixture defined at the outset. Moreover, we have found that applying the compounds I and the compounds II simultaneously, that is either together or separately, or applying the compounds I and the compounds II successively provides better control of harmful fungi than is possible with the individual compounds alone.

The formula I represents in particular imidazole derivatives of the formula I in which $R^1$ is halogen, in particular chlorine, and $R^2$ is tolyl, in particular p-tolyl.

Likewise, preference is given to compounds of the formula I in which $R^4$ is dimethylamino.

In addition, particular preference is given to the compound of the formula Ia (common name: cyazofamid). This compound is known from EP-A 298 196.

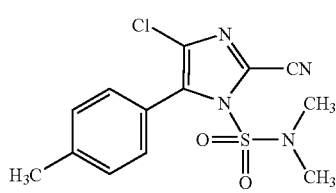

Furthermore, preference is given to compounds of the formula I in which $R^1$ and $R^2$ together with the bridging C=C double bond form a 3,4-difluoromethylenedioxyphenyl group.

In addition, preference is given to compounds of the formula I in which $R^4$ is 3,5-dimethylisoxazol-4-yl.

Particular preference is given to the compounds of the formula Ib in which X is halogen.

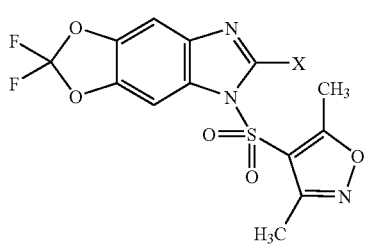

Halogen denotes fluorine, chlorine, bromine and iodine.

Particular preference is given to compounds of the formula Ib in which X is bromine or chlorine.

Preference is given to compounds of the formula II' [sic] which are S-configured in the amino acid moiety. These compounds correspond to the formula II':

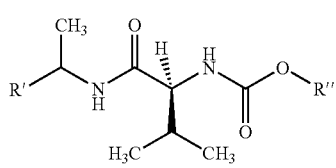

According to a further preferred embodiment, compounds of the formula II' are used where the carbon adjacent to the group R' is R-configured. These compounds correspond to the formula II":

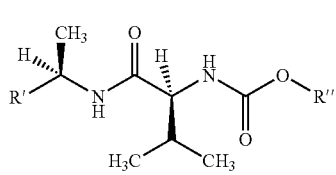

The formulae II' and II" represent in particular valinamides of the formulae IIa and IIb in which the substituents in each case correspond to one row of the table below:

| No.   | Formula | R    | R"           |
|-------|---------|------|--------------|
| II-1  | IIa     | Br   | CH(CH₃)₂     |
| II-2  | IIa     | Cl   | CH(CH₃)₂     |
| II-3  | IIa     | CH₃  | CH(CH₃)₂     |
| II-4  | IIa     | OCH₃ | CH(CH₃)₂     |
| II-5  | IIa     | Br   | CH(CH₃)CH₂CH₃ |
| II-6  | IIa     | Cl   | CH(CH₃)CH₂CH₃ |
| II-7  | IIa     | CH₃  | CH(CH₃)CH₂CH₃ |
| II-8  | IIa     | OCH₃ | CH(CH₃)CH₂CH₃ |
| II-9  | IIb     | F    | CH(CH₃)₂     |
| II-10 | IIb     | Cl   | CH(CH₃)₂     |
| II-11 | IIb     | Br   | CH(CH₃)₂     |
| II-12 | IIb     | F    | CH(CH₃)CH₂CH₃ |
| II-13 | IIb     | Cl   | CH(CH₃)CH₂CH₃ |
| II-14 | IIb     | Br   | CH(CH₃)CH₂CH₃ |

Particular preference is given to compounds II-3, II-9 and to compound II-15:

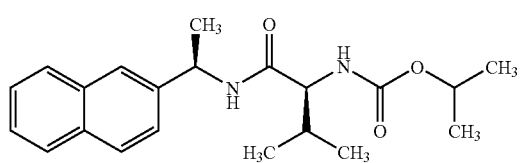

For the compounds II-1 to II-15, the configuration according to formula II' is preferred.

Particular preference is given to mixtures of the compounds of the formula Ia which comprise as second component II-3 (common name: iprovalicarb), II-9 or II-15.

When preparing the mixtures, it is preferred to employ the pure active compounds I and II, to which further active compounds against harmful fungi or against other pests, such as insects, arachnids or nematodes, or else herbicidal or growth-regulating active compounds or fertilizers can be admixed.

The mixtures of the compounds I and II, or the compounds I and II used simultaneously, together or separately, exhibit outstanding activity against a wide range of phytopathogenic fungi, in particular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and *Fusarium* and *Verticillium* species.

They can furthermore be employed in the protection of materials (for example the protection of wood), for example against *Paecilomyces variotii*.

The compounds I and II can be applied simultaneously, that is either together or separately, or successively, the sequence, in the case of separate application, generally not having any effect on the result of the control measures.

The compounds I and II are usually employed in a weight ratio of from 20:1 to 1:20, in particular from 10:1 to 1:10, preferably from 5:1 to 1:5.

Depending on the kind of effect desired, the application rates of the mixtures according to the invention are, in particular in agricultural crop areas, from 0.01 to 8 kg/ha, preferably 0.1 to 5 kg/ha, in particular 0.1 to 3.0 kg/ha.

The application rates of the compounds I are from 0.01 to 1 kg/ha, preferably 0.05 to 0.5 kg/ha, in particular 0.05 to 0.3 kg/ha.

Correspondingly, in the case of the compounds II, the application rates are from 0.01 to 1 kg/ha, preferably 0.02 to 0.5 kg/ha, in particular 0.05 to 0.3 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention or the compounds I and II can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by adding solvents and/or carriers. The formulations are usually admixed with inert additives, such as emulsifiers or dispersants.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol [sic] or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene [lacuna], lauryl alcohol polyglycol ether acetate, sorbitol esters, lignosulfite waste liquors or methylcellulose.

Powders, materials for broadcasting and dusts can be prepared by mixing or jointly grinding the compounds I or II or the mixture of the compounds I and II with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active compounds are employed in a purity of from 90% to 100%, preferably 95% to 100% (according to NMR spectrum or HPLC).

The compounds I and II, the mixtures, or the corresponding formulations, are applied by treating the harmful fungi, their habitat or the plants, seeds, soils, areas, materials or spaces to be kept free from them with a fungicidally effective amount of the mixture, or of the compounds I and II in the case of separate application.

Application can be effected before or after infection by the harmful fungi.

USE EXAMPLE

The synergistic activity of the mixtures according to the invention was demonstrated by the following experiments:

The active compounds, separately or together, were formulated as a 10% emulsion in a mixture of 63% by weight of cyclohexanone and 27% by weight of emulsifier, and diluted with water to the desired concentration.

Evaluation was carried out by determining the infected leaf areas in percent. These percentages were converted into efficacies. The efficacy (W) was calculated as follows using Abbot's formula:

$$W = (1-\alpha) \cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [R. S. Colby, Weeds 15, 20-22 (1967)] and compared with the observed efficacies.

$$E = x + y - x \cdot y/100 \qquad \text{Colby's formula}$$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b Use example: Protective activity against late blight of tomatoes caused by *Phytophthora infestans*

Leaves of potted plants of the cultivar "GroBe Fleischtomate St. Pierre" were sprayed to runoff point with an aqueous suspension which had been prepared from a stock solution comprising 10% of active compound, 85% of cyclohexanone and 5% of emulsifier. The next day, the leaves were infected with a cold aqueous zoospore suspension of *Phytophthora infestans* of a density of $0.25 \times 10^6$ spores/ml. The plants were then placed in a water-vapor-saturated chamber at temperatures between 18° C. and 20° C. After 6 days, the late blight on the untreated, but infected control plants had developed to such an extent that the infection could be determined visually in %.

TABLE A

Individual active compounds

| Example | Active compound | Active compound concentration in the spray liquor [ppm] | Efficacy in % of the untreated control |
|---------|-----------------|---------------------------------------------------------|----------------------------------------|
| 1 | Control (untreated) | (85% infection) | 0 |
| 2 | Ia | 0.2 | 82 |
|   |    | 0.1 | 70 |
|   |    | 0.05 | 53 |
| 3 | Ib.1 | 0.2 | 87 |
|   |      | 0.1 | 73 |
|   |      | 0.05 | 47 |
| 4 | II-3 | 0.2 | 70 |
|   |      | 0.1 | 53 |
|   |      | 0.05 | 29 |
| 5 | II-9 | 0.1 | 82 |
|   |      | 0.05 | 70 |

TABLE B

Combinations according to the invention

| Example | Active compound mixture concentration mixing ratio | Observed efficacy | Calculated efficacy*) |
|---------|----------------------------------------------------|-------------------|----------------------|
| 6 | Ia + II-3 0.1 + 0.1 ppm 1:1 | 100 | 86 |
| 7 | Ia + II-3 0.05 + 0.05 ppm 1:1 | 100 | 66 |
| 8 | Ia + II-3 0.1 + 0.05 ppm 2:1 | 100 | 79 |
| 9 | Ia + II-3 0.2 + 0.05 ppm 4:1 | 100 | 87 |

TABLE B-continued

Combinations according to the invention

| Example | Active compound mixture concentration mixing ratio | Observed efficacy | Calculated efficacy*) |
|---|---|---|---|
| 10 | Ia + II-3<br>0.05 + 0.1 ppm<br>1:2 | 100 | 78 |
| 11 | Ia + II-3<br>0.05 + 0.2 ppm<br>1:4 | 100 | 86 |
| 12 | Ia + II-9<br>0.05 + 0.05 ppm<br>1:1 | 100 | 86 |
| 13 | Ia + II-9<br>0.1 +0.05 ppm<br>2:1 | 100 | 91 |
| 14 | Ia + II-9<br>0.05 + 0.1 ppm<br>1:2 | 100 | 92 |
| 15 | Ib.1 + II-3<br>0.1 + 0.1 ppm<br>1:1 | 100 | 87 |
| 16 | Ib.1 + II-3<br>0.05 + 0.05 ppm<br>1:1 | 100 | 62 |
| 17 | Ib.1 + II-3<br>0.1 + 0.05 ppm<br>2:1 | 100 | 81 |
| 18 | Ib.1 + II-3<br>0.2 + 0.05 ppm<br>4:1 | 100 | 91 |
| 19 | Ib.1 + II-3<br>0.05 + 0.1 ppm<br>1:2 | 100 | 75 |
| 20 | Ib.1 + II-3<br>0.05 + 0.2 ppm<br>1:4 | 100 | 84 |
| 21 | Ib.1 + II-9<br>0.05 + 0.05 ppm<br>1:1 | 100 | 84 |
| 22 | Ib.1 + II-9<br>0.1 + 0.05 ppm<br>2:1 | 100 | 92 |
| 23 | Ib.1 + II-9<br>0.05 + 0.1 ppm<br>1:2 | 100 | 91 |
| 24 | Ib.1 + II-9<br>0.05 + 0.2 ppm<br>1:4 | 100 | 94 |

*) calculated using Colby's formula

The test results show that, for all mixing ratios, the observed efficacy is greater than the efficacy which had been calculated beforehand using Colby's formula.

We claim:

1. A fungicidal mixture, comprising
A) the imidazole derivative of the formula Ia

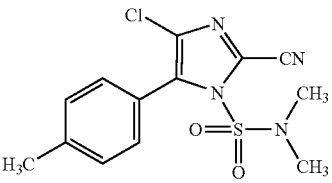

and
B) valinamides of the formula II,

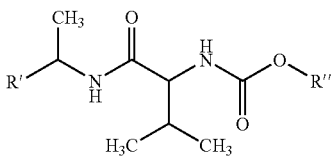

in which
R' is phenyl, which is substituted in the 4-position by halogen or $C_1$-$C_4$-alkoxy,
is 1- or 2-naphthyl, or
is benzothiazol-2-yl, which is substituted in the 6-position by halogen; and
R" is $C_3$-$C_4$-alkyl;
in a synergistically effective amount.

2. A fungicidal mixture as claimed in claim 1, wherein the weight ratio of the imidazole derivative Ia to the valinamides II is from 20:1 to 1:20.

3. A method for controlling harmful fungi, which comprises treating the harmful fungi, their habitat or plants, seeds, soils, areas, materials or spaces to be kept free from the fungi with the fungicidal mixture defined in claim 1.

4. A method as claimed in claim 3, wherein the imidazole derivative of the formula Ia is applied in an amount of from 0.01 to 2.5 kg/ha.

5. A method as claimed in claim 3, wherein the valinamides of the formula II are applied in an amount of from 0.01 to 10 kg/ha.

* * * * *